United States Patent
Joe

(10) Patent No.: US 10,428,307 B2
(45) Date of Patent: Oct. 1, 2019

(54) METHOD FOR CONVERTING MESENCHYMAL STEM CELLS INTO ENDOTHELIAL CELLS BY USING SPECIFIC TRANSCRIPTION FACTORS

(71) Applicant: THE CATHOLIC UNIVERSITY OF KOREA INDUSTRY-ACADEMIC COOPERATION FOUNDATION, Seoul (KR)

(72) Inventor: Young-Ae Joe, Seoul (KR)

(73) Assignee: The Catholic University of Korea Industry-Academic Cooperation Foundation (KR)

( * ) Notice: Subject to any disclaimer, the term of this patent is extended or adjusted under 35 U.S.C. 154(b) by 110 days.

(21) Appl. No.: 15/570,619

(22) PCT Filed: Apr. 29, 2016

(86) PCT No.: PCT/KR2016/004557
§ 371 (c)(1),
(2) Date: Oct. 30, 2017

(87) PCT Pub. No.: WO2016/175618
PCT Pub. Date: Nov. 3, 2016

(65) Prior Publication Data
US 2019/0055518 A1      Feb. 21, 2019

(30) Foreign Application Priority Data

Apr. 29, 2015   (KR) .................. 10-2015-0060259
Apr. 29, 2016   (KR) .................. 10-2016-0053144

(51) Int. Cl.
*C12N 5/0775*   (2010.01)
*C12N 15/85*    (2006.01)
*C12N 5/071*    (2010.01)

(52) U.S. Cl.
CPC ........... *C12N 5/0665* (2013.01); *C12N 5/069* (2013.01); *C12N 5/0668* (2013.01); *C12N 15/85* (2013.01); *C12N 2501/60* (2013.01); *C12N 2501/603* (2013.01); *C12N 2501/605* (2013.01); *C12N 2506/1346* (2013.01); *C12N 2510/00* (2013.01); *C12N 2740/15041* (2013.01); *C12N 2740/16043* (2013.01)

(58) Field of Classification Search
CPC .... C12N 5/0665; C12N 5/0668; C12N 15/85; C12N 2506/1346; C12N 2740/15041
See application file for complete search history.

(56) References Cited

U.S. PATENT DOCUMENTS

2014/0349398 A1    11/2014    Yu et al.

FOREIGN PATENT DOCUMENTS

CN    1546656     11/2004
CN    102776150   11/2012

OTHER PUBLICATIONS

Oram et al., Oncogene 29, 5796-5808, 2010.*
Cines et al., Blood, vol. 91, No. 10: pp. 3527-3561, May 15, 1998.*
Xu et al., Cell Stem Cell 16: 119-134, Feb. 5, 2015.*
Prasad, Stem Cells and Development,26(3): 154-165, 2017.*
Kim et al. Cell Stem Cell, 4(6): 472-476, 2009.*
Zhou et al., Cell Stem Cell, 4: 381-384, 2009.*
Crisan et al., Stem Cell Research & Therapy 2013, 4:95.*
Prasad et al. Regen. Med. 11(2), 181-191, 2016.*
Oswald et al., "Mesenchymal Stem Cells Can Be Differentiated Into Endothelial Cells In Vitro", Stem Cells 2004; 22: 377-384.
Han et al., "Direct Conversion of Adult Skin Fibroblasts to Endothelial Cells by Defined Factors", Circulation, 2014; 130: 1168-1178.

* cited by examiner

*Primary Examiner* — Thaian N Ton
(74) *Attorney, Agent, or Firm* — JHK Law; Joseph Hyosuk Kim

(57) ABSTRACT

The present invention relates to a method for converting mesenchymal stem cells into endothelial cells by using specific transcription factors and, more specifically, a method for converting mesenchymal stem cells into endothelial cells by using Oct4, Nanog, Tal1, and LMO2, which are specific transcription factors. According to the present invention, the method for converting adult cells or mesenchymal stem cells, which are adult stem cells, into endothelial cells was developed by selecting two types of genes, which are less directly related to cancer induction, among cell reprogramming factors and two types of transcription factors, which are not expressed or expressed at a low level in mesenchymal stem cells, among transcription factors related to vascular development, and combining all four transcription factors. The method can be applied in the production of endothelial cells for forming regenerative tissue in tissue engineering and ischemic disease therapy.

2 Claims, 4 Drawing Sheets
Specification includes a Sequence Listing.

[FIG. 1]
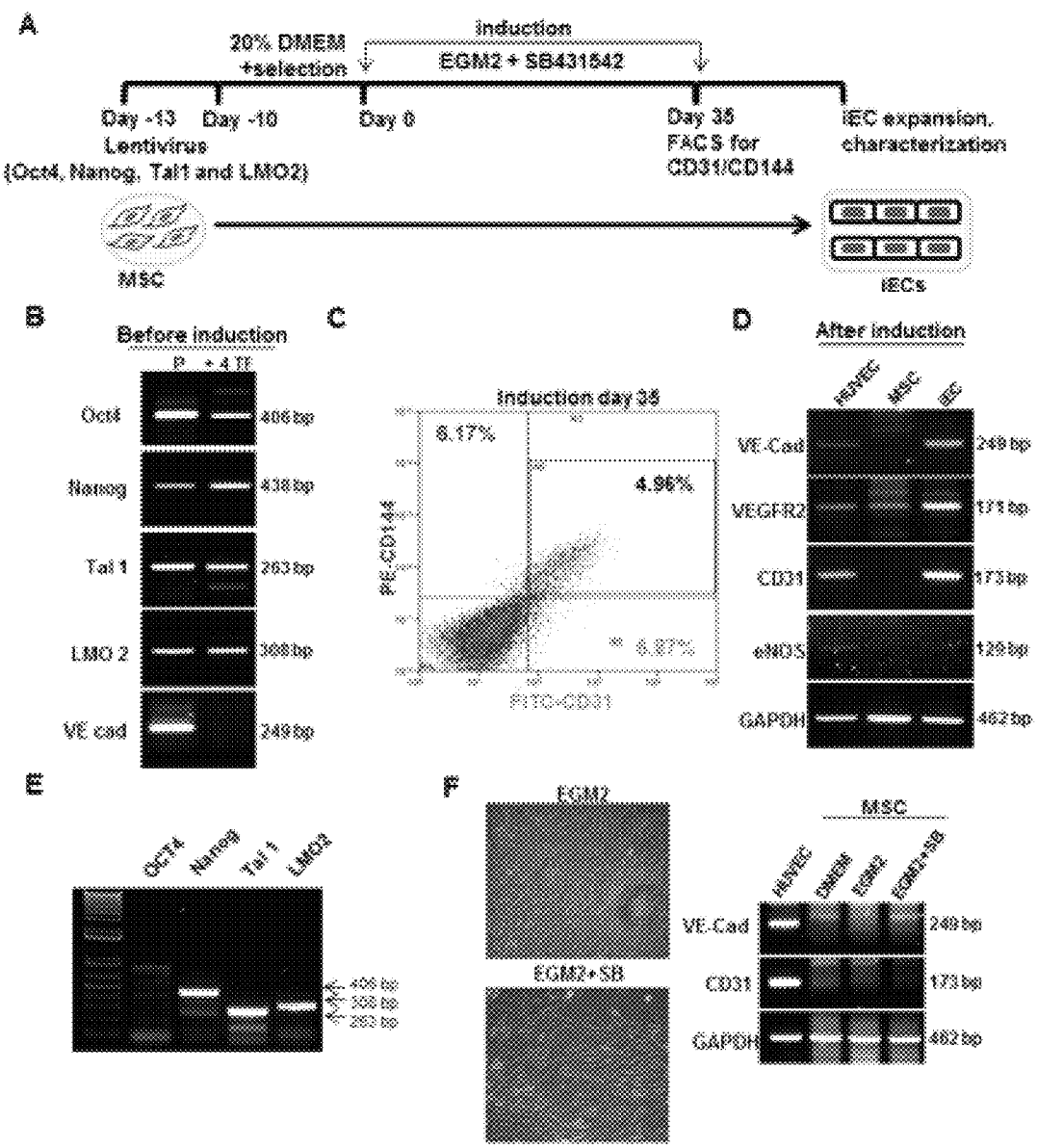

[FIG. 2]
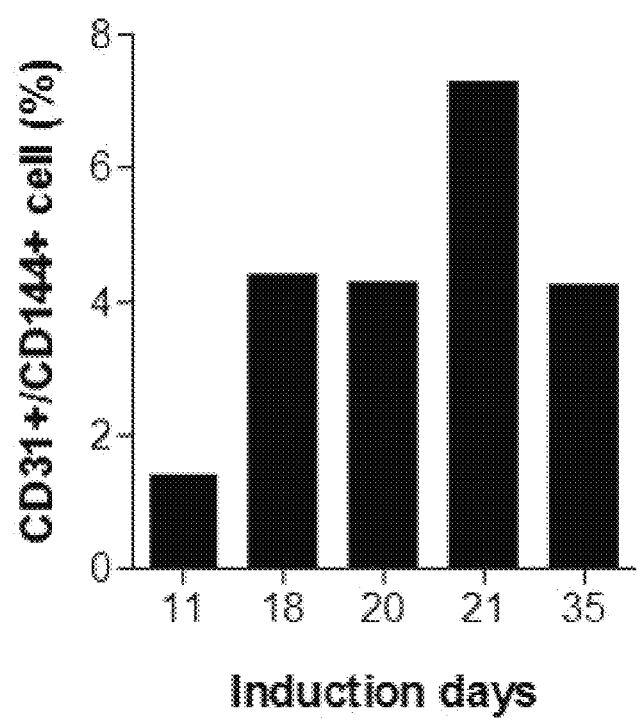

[FIG. 3]
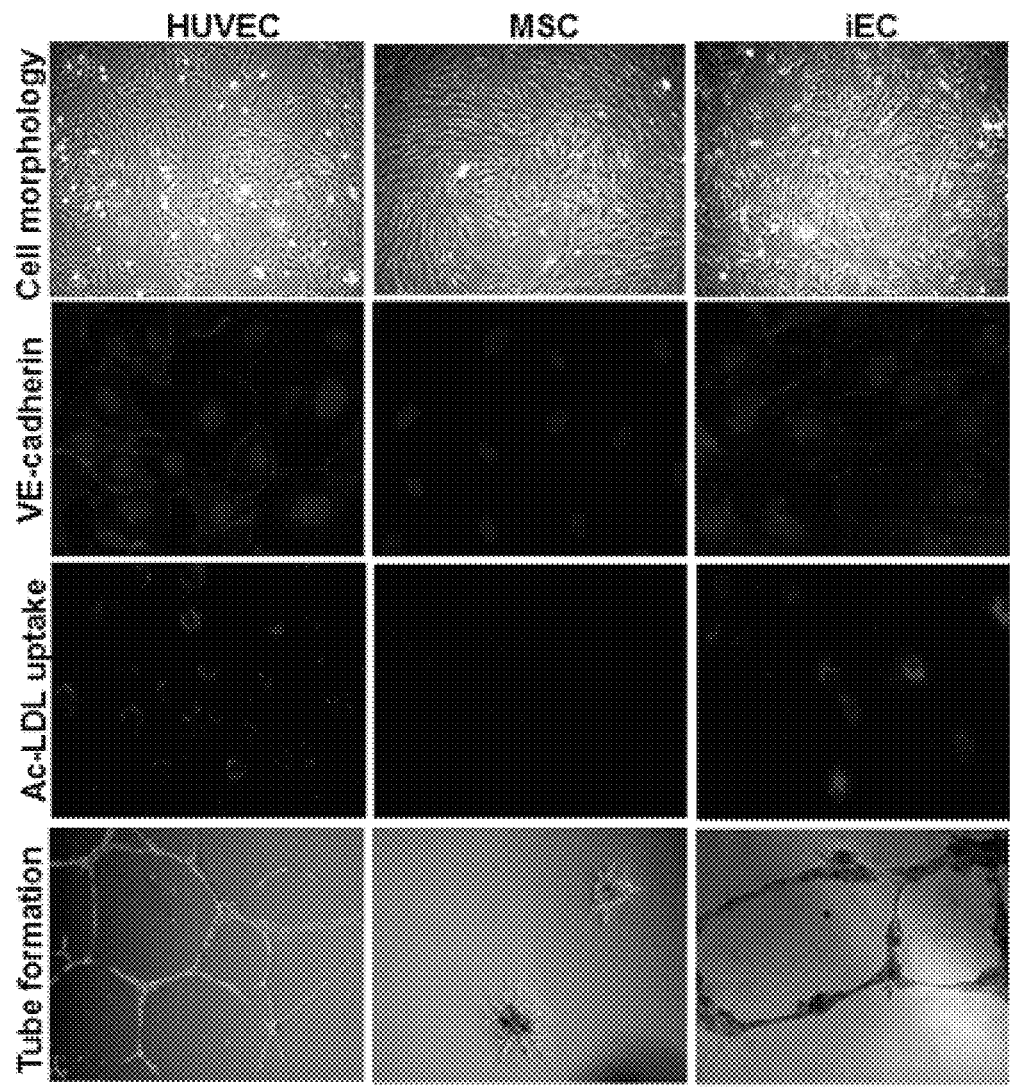

[FIG. 4]
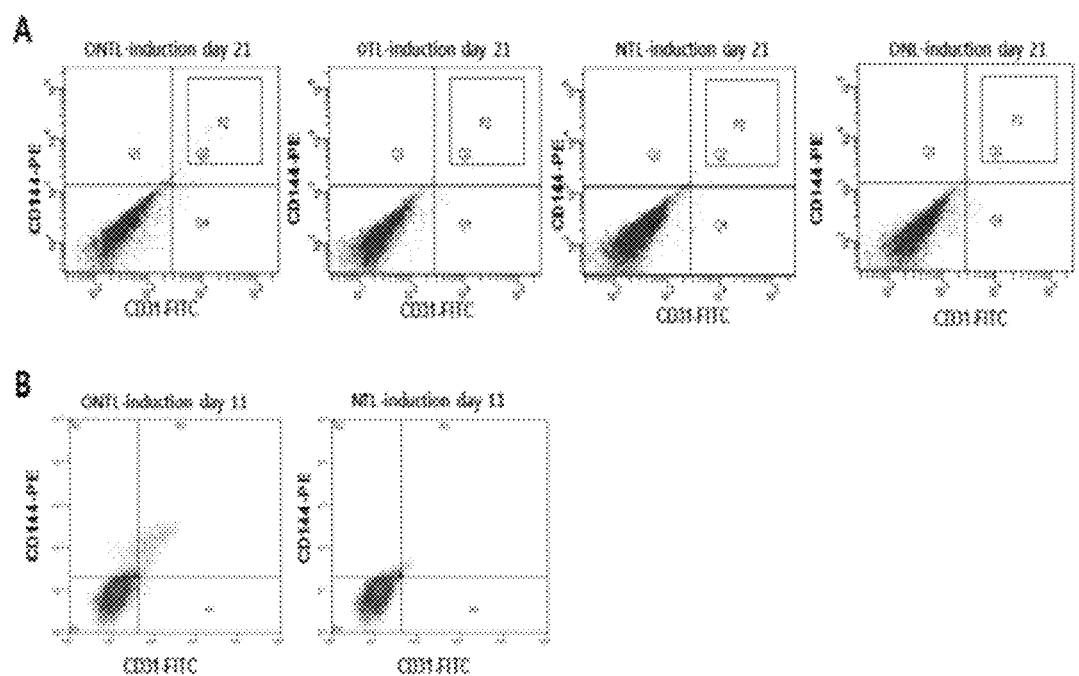

SEQUENCE LISTING

```
<160> NUMBER OF SEQ ID NOS: 8

<210> SEQ ID NO 1
<211> LENGTH: 1084
<212> TYPE: DNA
<213> ORGANISM: Artificial Sequence
<220> FEATURE:
<223> OTHER INFORMATION: Oct4 cDNA sequence

<400> SEQUENCE: 1
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag gctctgaggt gtgggggatt     180
cccccatgcc ccccgccgta tgagttctgt gggggatgg cgtactgtgg gccccaggtt     240
ggagtggggc tagtgcccca aggcggcttg gagacctctc agcctgaggg cgaagcagga     300 gtcgggtgg agagcaactc cgatgggcc tccccggagc cctgcaccgt cacccctggt     360
gccgtgaagc tggagaagga gaagctggag caaaacccgg aggagtccca ggacatcaaa     420
gctctgcaga aagaactcga gcaatttgcc aagctcctga agcagaagag gatcaccctg     480
ggatatacac aggccgatgt ggggctcacc ctgggggttc tatttgggaa ggtattcagc     540
caaacgacca tctgccgctt tgaggctctg cagcttagct tcaagaacat gtgtaagctg     600
cggcccttgc tgcagaagtg ggtggaggaa gctgacaaca atgaaaatct tcaggagata     660
tgcaaagcag aaaccctcgt gcaggcccga aagagaaagc gaaccagtat cgagaaccga     720
gtgagaggca acctggagaa tttgttcctg cagtgcccga aacccacact gcagcagatc     780
agccacatcg cccagcagct tgggctcgag aaggatgtgg tccgagtgtg gttctgtaac     840
cggcgccaga agggcaagcg atcaagcagc gactatgcac aacgagagga ttttgaggct     900
gctgggtctc ctttctcagg gggaccagtg tcctttcctc tggccccagg gccccatttt     960 ggtacccag gctatgggag ccctcacttc actgcactgt actcctcggt cccttccct    1020 gaggggaag ccttcccc tgtctccgtc accactctgg gctctcccat gcattcaaac    1080
tgag                                                               1084

<210> SEQ ID NO 2
<211> LENGTH: 918
<212> TYPE: DNA
<213> ORGANISM: Artificial Sequence
<220> FEATURE:
<223> OTHER INFORMATION: Nanog cDNA sequence

<400> SEQUENCE: 2
atgagtgtgg atccagcttg tccccaaagc ttgccttgct ttgaagcatc cgactgtaaa      60
```

```
gaatcttcac ctatgcctgt gatttgtggg cctgaagaaa actatccatc cttgcaaatg      120
tcttctgctg agatgcctca cacgagact gtctctcctc ttccttcctc catggatctg      180
cttattcagg acagccctga ttcttccacc agtcccaaag gcaaacaacc cacttctgca      240
gagaagagtg tcgcaaaaaa ggaagacaag gtcccggtca agaaacagaa gaccagaact      300
gtgttctctt ccacccagct gtgtgtactc aatgatagat ttcagagaca gaaataccctc     360 agcctccagc agatgcaaga actctccaac atcctgaacc tcagctacaa acaggtgaag      420
acctggttcc agaaccagag aatgaaatct aagaggtggc agaaaaacaa ctggccgaag      480
aatagcaatg gtgtgacgca gaaggcctca gcacctacct accccagcct ttactcttcc      540
taccaccagg gatgcctggt gaacccgact gggaaccttc caatgtggag caaccagacc      600
tggaacaatt caacctggag caaccagacc cagaacatcc agtcctggag caaccactcc      660
tggaacactc agacctggtg cacccaatcc tggaacaatc aggcctggaa cagtcccttc      720
tataactgtg gagaggaatc tctgcagtcc tgcatgcagt tccagccaaa ttctcctgcc      780
agtgacttgg aggctgcctt ggaagctgct ggggaaggcc ttaatgtaat acagcagacc      840
actaggtatt ttagtactcc acaaaccatg gatttattcc taaactactc catgaacatg      900
caacctgaag acgtgtga                                                   918

<210> SEQ ID NO 3
<211> LENGTH: 996
<212> TYPE: DNA
<213> ORGANISM: Artificial Sequence
<220> FEATURE:
<223> OTHER INFORMATION: Tal1 cDNA sequence

<400> SEQUENCE: 3
atgaccgagc ggccgccgag cgaggcggct cgcagtgacc cccagctaga gggacgggac       60
gcggccgagg ccagcatggc cccccccgcac ctggtcctgc tgaacggcgt cgccaaggag     120
acgagccgcg cggccgcagc ggagccccca gtcatcgaac tgggcgcgcg cggaggcccg     180 ggggcggcc ctgccggtgg gggcggcgcc gcgagagact taagggccg cgacgcggcg       240 acggccgaag cgcgccatcg ggtgccacc accgagctgt gcagacctcc cgggcccgcc      300
ccggcccccg cgcccgcctc ggttacagcg gagctgcccg gcgacggccg catggtgcag     360
ctgagtcctc ccgcgctggc tgcccccgcc gcccccggcc gcgcgctgct ctacagcctc     420
agccagccgc tggcctctct cggcagcggg ttctttgggg agccggatgc cttccctatg     480
ttcaccacca caatcgagt gaagaggaga ccttcccccct atgagatgga gattactgat      540
ggtccccaca ccaaagttgt gcggcgtatc ttcaccaaca gccgggagcg atggcggcag     600
cagaatgtga acgggccctt tgccgagctc gcaagctga tccccacaca tcccccggac      660
aagaagctca gcaagaatga gatcctccgc ctggccatga gtatatcaa cttcttggcc      720 aagctgctca atgaccagga ggaggaggggc acccagcggg ccaagactgg caaggaccct    780 gtggtgggg ctggtggggg tggaggtggg ggaggggggcg gcgcgccccc agatgacctc     840
ctgcaagacg tgctttcccc caactccagc tgcggcagct ccctggatgg ggcagccagc     900
ccggacagct acacggagga gccgcgcgcc aagcacacgg cccgcagcct ccatcctgcc     960
atgctgcctg ccgccgatgg agccggccct cggtga                              996

<210> SEQ ID NO 4
<211> LENGTH: 684
<212> TYPE: DNA
```

<213> ORGANISM: Artificial Sequence
<220> FEATURE:
<223> OTHER INFORMATION: LMO2 cDNA sequence

<400> SEQUENCE: 4

```
atggaaggga gcgcggtgac tgtccttgag cgcggagggg cgagctcgcc ggcggagcgc     60
cggagcaagc ggaggcgcag gagcggcggc gacggcggcg gcggcggcgg cgcccgagca    120
cccgaggggg tccgagcccc ggcagccggc cagccccgcg ccacaaaggg agcgcccccg    180
ccgcccggca ccccgcctcc ctccccaatg tcctcggcca tcgaaaggaa gagcctggac    240
ccttcagagg aaccagtgga tgaggtgctg cagatccccc catccctgct gacatgcggc    300
ggctgccagc agaacattgg ggaccgctac ttcctgaagg ccatcgacca gtactggcac    360
gaggactgcc tgagctgcga cctctgtggc tgccggctgg gtgaggtggg cggcgcctc     420
tactacaaac tgggccggaa gctctgccgg agagactatc tcaggctttt tgggcaagac    480
ggtctctgcg catcctgtga caagcggatt cgtgcctatg agatgacaat gcgggtgaaa    540
gacaaagtgt atcacctgga atgtttcaaa tgcgccgcct gtcagaagca tttctgtgta    600
ggtgacagat acctcctcat caactctgac atagtgtgcg aacaggacat ctacgagtgg    660
actaagatca tgggatgat atag                                            684
```

<210> SEQ ID NO 5
<211> LENGTH: 360
<212> TYPE: PRT
<213> ORGANISM: Artificial Sequence
<220> FEATURE:
<223> OTHER INFORMATION: Oct4 amino acid sequence

<400> SEQUENCE: 5

```
Met Ala Gly His Leu Ala Ser Asp Phe Ala Phe Ser Pro Pro Pro Gly
  1               5                  10                  15

Gly Gly Gly Asp Gly Pro Gly Gly Pro Glu Pro Gly Trp Val Asp Pro
                 20                  25                  30

Arg Thr Trp Leu Ser Phe Gln Gly Pro Pro Gly Gly Pro Gly Ile Gly
             35                  40                  45

Pro Gly Val Gly Pro Gly Ser Glu Val Trp Gly Ile Pro Pro Cys Pro
         50                  55                  60

Pro Pro Tyr Glu Phe Cys Gly Gly Met Ala Tyr Cys Gly Pro Gln Val
 65                  70                  75                  80

Gly Val Gly Leu Val Pro Gln Gly Gly Leu Glu Thr Ser Gln Pro Glu
                 85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205
```

```
Glu Glu Ala Asp Asn Asn Glu Asn Leu Gln Glu Ile Cys Lys Ala Glu
    210                 215                 220

Thr Leu Val Gln Ala Arg Lys Arg Lys Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
                275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 6
<211> LENGTH: 304
<212> TYPE: PRT
<213> ORGANISM: Artificial Sequence
<220> FEATURE:
<223> OTHER INFORMATION: Nanog amino acid sequence

<400> SEQUENCE: 6

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205
```

```
Gln Thr Gln Asn Ile Gln Ser Trp Ser Asn His Ser Trp Asn Thr Gln
    210                 215                 220
Thr Trp Cys Thr Gln Ser Trp Asn Asn Gln Ala Trp Asn Ser Pro Phe
225                 230                 235                 240
Tyr Asn Cys Gly Glu Glu Ser Leu Gln Ser Cys Met Gln Phe Gln Pro
                245                 250                 255
Asn Ser Pro Ala Ser Asp Leu Glu Ala Ala Leu Glu Ala Ala Gly Glu
            260                 265                 270
Gly Leu Asn Val Ile Gln Gln Thr Arg Tyr Phe Ser Thr Pro Gln
        275                 280                 285
Thr Met Asp Leu Phe Leu Asn Tyr Ser Met Asn Met Gln Pro Glu Asp
290                 295                 300
```

<210> SEQ ID NO 7
<211> LENGTH: 331
<212> TYPE: PRT
<213> ORGANISM: Artificial Sequence
<220> FEATURE:
<223> OTHER INFORMATION: Ta11 amino acid sequence

<400> SEQUENCE: 7

```
Met Thr Glu Arg Pro Pro Ser Glu Ala Ala Arg Ser Asp Pro Gln Leu
1               5                   10                  15
Glu Gly Arg Asp Ala Ala Glu Ala Ser Met Ala Pro Pro His Leu Val
                20                  25                  30
Leu Leu Asn Gly Val Ala Lys Glu Thr Ser Arg Ala Ala Ala Ala Glu
            35                  40                  45
Pro Pro Val Ile Glu Leu Gly Ala Arg Gly Gly Pro Gly Gly Gly Pro
        50                  55                  60
Ala Gly Gly Gly Ala Ala Arg Asp Leu Lys Gly Arg Asp Ala Ala
65                  70                  75                  80
Thr Ala Glu Ala Arg His Arg Val Pro Thr Thr Glu Leu Cys Arg Pro
                85                  90                  95
Pro Gly Pro Ala Pro Ala Pro Ala Pro Ala Ser Val Thr Ala Glu Leu
            100                 105                 110
Pro Gly Asp Gly Arg Met Val Gln Leu Ser Pro Ala Leu Ala Ala
        115                 120                 125
Pro Ala Ala Pro Gly Arg Ala Leu Leu Tyr Ser Leu Ser Gln Pro Leu
130                 135                 140
Ala Ser Leu Gly Ser Gly Phe Phe Gly Glu Pro Asp Ala Phe Pro Met
145                 150                 155                 160
Phe Thr Thr Asn Asn Arg Val Lys Arg Arg Pro Ser Pro Tyr Glu Met
                165                 170                 175
Glu Ile Thr Asp Gly Pro His Thr Lys Val Val Arg Arg Ile Phe Thr
            180                 185                 190
Asn Ser Arg Glu Arg Trp Arg Gln Gln Asn Val Asn Gly Ala Phe Ala
        195                 200                 205
Glu Leu Arg Lys Leu Ile Pro Thr His Pro Pro Asp Lys Lys Leu Ser
210                 215                 220
Lys Asn Glu Ile Leu Arg Leu Ala Met Lys Tyr Ile Asn Phe Leu Ala
225                 230                 235                 240
Lys Leu Leu Asn Asp Gln Glu Glu Gly Thr Gln Arg Ala Lys Thr
                245                 250                 255
Gly Lys Asp Pro Val Val Gly Ala Gly Gly Gly Gly Gly Gly Gly
            260                 265                 270
```

```
                                        -continued

Gly Gly Ala Pro Pro Asp Asp Leu Leu Gln Asp Val Leu Ser Pro Asn
            275                 280                 285

Ser Ser Cys Gly Ser Ser Leu Asp Gly Ala Ala Ser Pro Asp Ser Tyr
        290                 295                 300

Thr Glu Glu Pro Ala Pro Lys His Thr Ala Arg Ser Leu His Pro Ala
305                 310                 315                 320

Met Leu Pro Ala Ala Asp Gly Ala Gly Pro Arg
                    325                 330

<210> SEQ ID NO 8
<211> LENGTH: 208
<212> TYPE: PRT
<213> ORGANISM: Artificial Sequence
<220> FEATURE:
<223> OTHER INFORMATION: LMO2 amino acid sequence

<400> SEQUENCE: 8

Met Glu Gly Ser Ala Val Thr Val Leu Glu Arg Gly Gly Ala Ser Ser
1               5                   10                  15

Pro Ala Glu Arg Arg Ser Lys Arg Arg Arg Ser Gly Gly Asp Gly
            20                  25                  30

Gly Gly Gly Gly Ala Arg Ala Pro Glu Gly Val Arg Ala Pro Ala
            35                  40                  45

Ala Gly Gln Pro Arg Ala Thr Lys Gly Ala Pro Pro Pro Pro Gly Thr
        50                  55                  60

Pro Pro Pro Ser Pro Met Ser Ser Ala Ile Glu Arg Lys Ser Leu Asp
65                  70                  75                  80

Pro Ser Glu Glu Pro Val Asp Glu Val Leu Gln Ile Pro Pro Ser Leu
                85                  90                  95

Leu Thr Cys Gly Gly Cys Gln Gln Asn Ile Gly Asp Arg Tyr Phe Leu
            100                 105                 110

Lys Ala Ile Asp Gln Tyr Trp His Glu Asp Cys Leu Ser Cys Asp Leu
            115                 120                 125

Cys Gly Cys Arg Leu Gly Glu Val Gly Arg Arg Leu Tyr Tyr Lys Leu
        130                 135                 140

Gly Arg Lys Leu Cys Arg Arg Asp Tyr Leu Arg Leu Phe Gly Gln Asp
145                 150                 155                 160

Gly Leu Cys Ala Ser Cys Asp Lys Arg Ile Arg Ala Tyr Glu Met Thr
                165                 170                 175

Met Arg Val Lys Asp Lys Val Tyr His Leu Glu Cys Phe Lys Cys Ala
            180                 185                 190

Ala Cys Gln Lys His Phe Cys Val Gly Asp Arg Tyr Leu Leu Ile Asn
            195                 200                 205
```

METHOD FOR CONVERTING MESENCHYMAL STEM CELLS INTO ENDOTHELIAL CELLS BY USING SPECIFIC TRANSCRIPTION FACTORS

TECHNICAL FIELD

The present invention relates to a method for converting mesenchymal stem cells into endothelial cells by using specific transcription factors and, more specifically, a method for converting mesenchymal stem cells into endothelial cells by using Oct4, Nanog, Tal1, and LMO2, which are specific transcription factors.

BACKGROUND ART

The production of endothelial cells from pluripotent stem cells such as embryonic stem cells and induced pluripotent stem cells is important because it can be applied to the treatment of ischemic diseases which requires angiogenesis. Endothelial cells are also essential to provide important vascular networks in the field of regenerating tissues such as liver tissues. Although many studies for the induction of differentiation of embryonic stem cells or induced pluripotent stem cells into endothelial cells have been carried out, new cells obtained from these cells are likely to have possibility of cancer induction and to be incapable of differentiation so that a transdifferentiation to endothelial cells by partial reprogramming of mature somatic cells such as fibroblasts can be an alternative [Graf, T. et al., Nature., 2009].

In fact, mouse embryonic fibroblasts have been successfully converted to muscle cells by the MyoD gene and 5-azacytidine [Davis, R. L, et al., Cell, 1987]. Ngn3, Pdx1, and Mafa genes have been introduced into pancreatic exocrine cells, thereby converting into beta cell-like cells that secrete insulin [Zhou, Q., et al., Nature, 2008].

In the case of endothelial cells, Ginsberg et al. firstly introduced ETS transcription factors ETV2, FLI1, and ERG1 into human midgestation c-Kit-linease-committed amniotic cells in 2012 and reported that the induced culture was performed in EGM2 medium in the presence of TGF-beta inhibitor, thereby converting into cells which exhibit the property of endothelial cells (Ginsberg, M., et al., Cell, 2012). These cells were observed to form stable blood vessels in Matrigel plug and regenerated liver tissue. Afterwards, it was reported that only one ETV2 gene could be introduced into human skin fibroblasts and converted into cells showing the characteristics of venous endothelial cells [Morita, R., et al., Proc Natl Acad Sci USA, 2015].

Further, innate immunity was stimulated using a toll-like receptor 3 (TLR3) agonist so that fibroblasts were converted into cells showing the characteristics of endothelial cells [Sayed, N., et al., Circulation, 2015]. Two kinds of genes, Oct4 and Klf4 were introduced to convert into cells expressing endothelial cell characteristics [Li, J., et al., Arterioscler Thromb Vasc Biol, 2013].

In addition, it was tried that Oct4, Sox2, Klf4, and c-Myc which are Yamanaka factors 4 were introduced, but partial reprogramming was performed without induction of iPS production stage, thereby converting into endothelial cells [Margariti, A., et al., Proc Natl Acad Sci 2012]. In the present invention, two genes that are not directly related to cancer induction are selected among the reprogramming factors, and two transcription factors that are expressed at a low level or not expressed in mesenchymal stem cells derived from the umbilical cord are selected among the transcription factors related to vascular development. Thus, a method has been developed to convert adult somatic cells or mesenchymal stem cells (MSCs) which are adult stem cells into endothelial cells by combining these four transcription factors.

DISCLOSURE

Technical Problem

An object of the present invention is to provide a novel method for converting mesenchymal stem cells into endothelial cells.

Another object of the present invention is to provide a novel composition for converting mesenchymal stem cells into endothelial cells.

Still another object of the present invention is to provide a composition for tissue regeneration, which includes endothelial cells as an active ingredient, which is obtained by the method of the present invention.

Yet another object of the present invention is to provide a cell therapy composition for the treatment of ischemic diseases, which includes endothelial cells as an active ingredient, which is obtained by the method of the present invention.

Technical Solution

In order to achieve the objects as described above, the present invention provides a method of converting mesenchymal stem cells into endothelial cells, including: the step of introducing Oct4, Nanog, Tal1, and LMO2 genes or a protein encoded by the genes into the mesenchymal stem cells.

According to an embodiment of the present invention, the Oct4, Nanog, Tal1, and LMO2 genes may be transduced into the mesenchymal stem cells using a lentiviral vector.

According to an embodiment of the present invention, the Oct4 gene may be represented by SEQ ID NO: 1, the Nanog gene may be represented by SEQ ID NO: 2, the Tal1 gene may be represented by SEQ ID NO: 3, and the LMO2 gene may be represented by SEQ ID NO: 4.

Further, the present invention provides a composition for differentiation induction of mesenchymal stem cells into endothelial cells, including Oct4, Nanog, Tal1 and LMO2 genes or a protein encoded by the genes.

Further, the present invention provides a composition for tissue regeneration, including endothelial cells, which are obtained by the method as described above, as an active ingredient.

Further, the present invention provides a cell therapy composition for treating ischemic diseases, including endothelial cells, which are obtained by the method as described above, as an active ingredient.

Advantageous Effects

According to the present invention, a method has been developed to select two genes that are not directly related to cancer induction among the reprogramming factors and two transcription factors that are expressed at a low level or not expressed in mesenchymal stem cells among the transcription factors related to vascular development and to combine these four transcription factors, thereby converting adult somatic cells or mesenchymal stem cells which are adult stem cells into endothelial cells. The method can be applied

DESCRIPTION OF DRAWINGS

FIG. 1 illustrates the conversion of endothelial cells (EC) by the introduction of Oct4, Nanog, Tal1, and LMO2 genes. FIG. 1A illustrates a schematic diagram for the induction of MSC into endothelial cells. FIG. 1B illustrates the results of gene expression, which was confirmed with RT-PCR, after the introduction of Oct4, Nanog, Tal1, and LMO2 genes using lentiviral system for the induction of umbilical cord-derived MSC into endothelial cells. FIG. 1C illustrates the results of FACS analysis of cells (iEC) positive for CD31/CD144, which is an endothelial cell marker, after induction into endothelial cells. FIG. 1D illustrates the results of expression patterns of an endothelial cell marker, which was analyzed with RT-PCR, after iECs, which were induced into endothelial cells, were subcultured and expanded. FIG. 1E illustrates the results of expression patterns of Oct4, Nanog, Tal1, and LMO2 genes, which were analyzed with RT-PCR, after the expansion of iECs. FIG. 1F illustrates the results of exhibiting no conversion to endothelial cells when culturing MSC in EGM2 and endothelial cell-derived medium (EGM2+10 µM SB431542) without gene transfer.

FIG. 2 illustrates the results of examining the reproducibility and conversion rate of CD31/CD144 positive cells while repeating experiments with changing of culture time, in which MSC is converted into EC by Oct4, Nanog, Tal1, and LMO2.

FIG. 3 illustrates the results of ac-LDL uptake and tube formation after the expansion of the converted iEC and then the examination of the expression of VE-cadherin by immunofluorescence.

FIG. 4A illustrates the optimal gene combinations required for the conversion from WJ-MSC to endothelial cells. FIG. 4B illustrates the results of repeated experiments. In FIGS. 4A and 4B, ONTL represents a group using a combination of Oct4, Nanog, Tal1 4, and LMO2, OTL represents a group using a combination of Oct4, Tal1 4, and LMO2, NTL represents a group using a combination of Nanog, Tal1 4, and LMO2, and ONL represents a group using a combination of Oct4, Nanog, and LMO2.

BEST MODES OF THE INVENTION

Tal1 and LMO2 are known as major modulators of hematopoiesis and endothelial cell transcription. Human umbilical cord-derived mesenchymal stem cells were transduced with recombinant lentiviruses capable of delivering the cDNAs of Oct4, Nanog, Tal1, and LMO2 (See FIG. 1A) and cultured in a medium with blasticidin (350 ng/ml) and puromycin (350 ng/ml) for 10 days to select only transduced cells. RT-PCR was performed using total RNA. It was confirmed that these four genes were expressed in selected cells (See FIG. 1B). Then, these cells were cultured in EGM2 including SB431542 (10 µM) which is TGF inhibitor for 35 days to induce conversion to endothelial cells. FACS analysis of these cells confirmed an induced cell population including 4.96% of CD31+VE-cadherin+ cells (See FIG. 1C). These CD31+VE-cadherin+ cells were sorted by FACS and cultured in the same medium. PCR analysis of these cultured cells (iEC) leads to analyze endothelial genes of VE-cadherin, VEGFR2, CD31, and eNOS. As a result, VE-cadherin, VEGFR2, CD31, and eNOS were detected in cultured iEC cells as in HUVEC (See FIG. 1D). Analysis of Oct 4, Nanog, Tal1, and LMO2 gene expression in cultured iEC revealed the expression of Nanog, Tal1, and LMO2 except Oct 4 (See FIG. 1E). In contrast, it was shown that culture of MSCs without the transduction of these four transcription factors in the same induction medium did not induce conversion to EC cells (See FIG. 1F). Direct conversion of MSC to EC by these four factors could be confirmed in repeated experiments. Even on induction on the 11th day, conversion to EC cells occurred (See FIG. 2). It was confirmed that CD31 and CD144 positive cells ranged from 1.4% to 7%.

For the detailed analysis of the characteristics of iEC, immunofluorescence analysis of these cells revealed that VE-Cadherin was expressed around the cells as in HUVEC. In contrast to MSC, these cells had an ability of DiI-labeled ac-LDL uptake, indicating that they have endothelial cell characteristics.

Lastly, the present inventors have examined whether a tube-like structure may be formed in these induced cells. As illustrated in FIG. 3, the tube-like structure is formed on Matrigel at 20 hours in these cells as in HUVEC, in contrast to MSC.

Through the above results, the present inventors confirmed that reprogramming of MSC and adult cells into endothelial cells may be performed by Oct4, Nanog, Tal1, and LMO2.

Further, the present inventors confirmed that MSC and adult cells may be efficiently converted into endothelial cells only when all four genes of Oct4, Nanog, Tal1, and LMO2 are used as described above. According to one embodiment of the present invention, degree of endothelial cell conversion according to the gene combination was analyzed for a group in which three genes of Oct4, Tal1, and LMO2 (OTL) are introduced, a group in which three genes of Nanog, Tal1, and LMO2 (NTL) are introduced, a group in which three genes of Oct4, Nanog, and LMO2 (ONL) are introduced, and a group in which four genes of Oct4, Nanog, Tal1, and LMO2 are introduced.

As a result, as illustrated in FIG. 4, it was confirmed that cells were transformed into CD31/CD144 positive cells on the group in which four genes including Oct4, Nanog, LMO2, and Tal1 were introduced. However, it was confirmed that cells were not transformed into CD31/CD144 positive cells on the combination in which three genes of Oct4, Tal1, LMO2 (OTL), Nanog, Tal1, and LMO2, (NLT), or Oct4, Nanog, and LMO2 (ONL) were introduced.

Therefore, as a result, the present invention found that four special genes such as Oct4, Nanog, LMO2, and Tal1 should be introduced to completely convert MSC and adult cells into endothelial cells.

In the present invention, 4 genes, such as, Oct4, Nanog, LMO2, and Tal1, respectively, introduced for endothelial cell conversion are preferably Oct4 gene represented by SEQ ID NO: 1, Nanog gene represented by SEQ ID NO: 2, LMO2 gene represented by SEQ ID NO: 3 and Tal1 represented by SEQ ID NO: 4.

In addition, introduction of these genes into cells may be performed using any gene introduction technique known in the art. Lentiviral vectors are used in one embodiment of the present invention.

The endothelial cells obtained by the method as described above can be applied to the production of endothelial cells (EC) for constituting regenerated tissues in tissue engineering and treatment of ischemic diseases.

Accordingly, the present invention may provide a composition for regenerating a tissue including the endothelial cells obtained by the method of the present invention as an active ingredient. Further, the present invention may provide provides a composition for a cell therapy agent for treatment of ischemic diseases, which includes endothelial cells obtained by the method of the present invention as an active ingredient.

According to the present invention, endothelial cells converted from stem cells may be used as a cell therapy agent for tissue regeneration or treatment of ischemic diseases. In the case of tissue regeneration, the endothelial cells converted in the present invention may be used in a portion corresponding to the endothelial cells in terms of tissue structure.

MODES OF THE INVENTION

Hereinafter, the present invention will be described in more detail with reference to Embodiments. These embodiments are for further illustrating the present invention, and the scope of the present invention is not limited to these embodiments.

Embodiment 1

Conversion to Endothelial Cells by the Introduction of Oct4, Nanog, Tal1, and LMO2 Genes 1-1. Cell Culture and Reagent Preparation Human umbilical vein endothelial cells (HUVEC) were isolated from human blood vessels according to the method described by Jaffe, et al. HUVEC cells were cultured in M199 medium including 20% FBS (Invitrogen), 30 μg/ml endothelial cell growth supplements (ECGS, BD Biosciences), 90 μg/ml heparin, 1% antibiotic. iEC was cultured in EGM2 medium (Lonza) added with 10 μM SB431542 (Sigma), and mesenchymal stem cells (MSC) derived from umbilical cord were cultured in DMEM (Invitrogen) medium including 20% FBS and 1% antibiotic. Human umbilical cord samples were collected in accordance with the procedure approved by the Clinical Trial Evaluation Committee, Catholic University (project no. MC13TISI0078, MC12TISI0094).

1-2. Lentiviral Vectors and Transduction

Lentiviral vectors carrying Nanog, Tal1, and LMO2 were purchased from GeneCopoeia (USA), and Oct4 vectors were obtained from Won-Hee Suh, professor of Ajou University.

On the day before transfection, 293FT cells were plated on a 10 cm tissue culture plate, in order for the cell density to reach about 90% to 95% on the day of transfection. To prepare lentivirus, psi-EF1-Bls-hOct4, psi-EF1-Puro-hNanog, psi-EF1-Puro-hTaL1, and psi-EF1-Puro-hLMO2 (Genecopoeia; 3 for each plasmid), which are the desired vector plasmids, were mixed with 9 μg of ViraPowerPackaging Mix and 12 μg of Lipofectamine 2000 complex and then were added to 293FT cells. After overnight incubation at 37° C. and 5% $CO_2$, the medium was replaced with 293FT medium without antibiotics. The culture supernatant was collected 48 hours after the medium change. The virus supernatant was filtered through a 0.45 μm PVDF filter to remove the cells, and the virus stock was stored at −80° C. MSC ($5 \times 10^4$/well) was plated for 24 hours and infected with 5 MOI in 10% FBS-DMEM medium including 8 μg/ml polybrene (Sigma-Aldrich). After 24 hours, the medium including the virus was replaced with fresh DMEM medium added with 20% FBS and penicillin/streptomycin and then cultured for two days. The cells were then cultured for ten days in a medium including blasticidin (350 ng/ml) and puromycin (350 ng/ml), and the transfected cells were selected (See FIG. 1A).

1-3. Induction of MSC Transduced with Lentivirus into Endothelial Cells

MSC cells transduced with lentivirus were cultured in a gelatin-coated plate including endothelial cell growth medium EGM2 and 10 μM SB431542 to induce conversion into endothelial cells. The medium was replaced every two days. After three days to five days, the cells were split at 1:2 when the density of cells became 90%. The cells were cultured for 11 days to 35 days, and then iEC was isolated by FACS.

1-4. RNA Extraction and RT-PCR

Total RNA was extracted from cultured cells using Trizol reagent (Invitrogen). cDNA synthesis for RT-PCR was carried out using SuperScript synthesis system (Enzynomics) in accordance with the manufacturer's instructions. Each gene was amplified by PCR using the primer set described in Table 1. The PCR conditions for the synthesized cDNA were as follows: a total 30 cycles of 95° C. for 7 minutes (initial denaturation), 95° C. for 1 minute (denaturation), 54° C. to 60° C. for 1 minute (annealing) and 72° C. for 1 minute (extension) and 72° C. for 10 minutes (last extension). PCR products were analyzed by 1.0% agarose-gel electrophoresis, and DNA bands were visualized by SYBR safe DNA gel staining (Invitrogen).

TABLE 1

| Name | Forward | Reserve | Accession no. |
| --- | --- | --- | --- |
| Oct4 | AGGAGATATGCAAAGCAGAA | AGAGTGGTGACGGAGACAG | NM_002701 |
| Nanog | ATCCAGCTTGTCCCCAAAG | ATTTCATTCTCTGGTTCTGG | NM_024865.2 |
| Tal1 | TCACCACCAACAATCGAGTGAAGAGG | CTCCTCCTGGTCATTGAGCAGCTTGG | NM_003189.2 |
| LMO2 | TCCCCAATGTCCTCGGCCAT | ATCCGCTTGTCACAGGAT | NM_005574.3 |
| CD31 | ATGATGCCCAGTTTGAGGTC | GACGTCTTCAGTGGGGTTGT | NM_000442.4 |
| VE-ead | CCCTACCAGCCCAAAGTGTG | CGACTTGGCATCCCATTGTC | NM_001795.3 |
| VEGFR2 | GCGATGGCCTCTTCTGTAAG | ACACGACTCCATGTTGGTCA | EU826563.1 |
| eNOS | TGATGGCGAAGCGAGTGAA | ACTCATCCATACACAGGACCCG | NM_000603.4 |

It was examined whether Oct4, Nanog, Tal1, and LMO2 were expressed after transduction with lentivirus using RT- PCR as described above. It was confirmed that these genes were expressed (See FIG. 1B). Meanwhile, these cells were induced to differentiate into endothelial cells and then were separated by FACS sorting. The separated iECs were subcultured and amplified, and then the endothelial marker expression patterns were analyzed by RT-PCR as described above. As a result, it was confirmed that VE-cadherin, VEGFR2, CD31, and eNOS were expressed like HUVEC (See FIG. 1D). Expression of Nanog, Tal1, and LMO2 was confirmed by RT-PCR (See FIG. 1E).

1-5. FACS Analysis

After induction of differentiation into endothelial cells, FACS analysis was performed to confirm the cells positive to CD31/CD144, which are endothelial cell markers.

For this purpose, cells were collected and stained with PE-conjugated VE-cadherin antibody (1:400; BD Biosciences) or FITC-conjugated CD31 antibody (1:400; BD Biosciences) for 30 minutes in ice. The samples were analyzed with a FACSAria III cell analyzer (BD Biosciences). Data were analyzed with BD CellQuest Pro software (version 5.2.1). For identification of CD31+/CD144+ cells, the cells were transduced with the virus and then were cultured for 35 days in the endothelial differentiation induction medium. Then, the cells were collected and analyzed by FACS Beckman coulter cell sorter (BD Biosciences). Data were analyzed with FACS summit software (version 6.1.3). CD31+/CD144+ iECs were separated by FACS and subsequently cultured in EGM2 including 10 µM SB431542 using plates coated with 1% gelatin.

As illustrated in FIG. 1C, the result confirms that cells (iEC) positive for CD31/CD144 which was an endothelial cell marker were present at a ratio of 4.96%.

Embodiment 2

Review of Reproducibility and Rate for Conversion of MSC into EC by Oct4, Nanog, Tal1, and LMO2

While four genes were introduced to induce the differentiation of endothelial cells in the same experimental scheme as in Embodiment 1, the experiments were repeatedly performed by changing the incubation time in the endothelial cell induced medium. Therefore, it was examined whether CD31/CD144 positive cells were reproducibly prepared and how the conversion rates were changed.

For identification of CD31+/CD144+ cells, the cells were transduced with the virus and then were cultured for 11 days to 35 days in the endothelial differentiation induction medium. Then, the cells were collected and analyzed by FACS Beckman coulter cell sorter (BD Biosciences). Data were analyzed with FACS summit software (version 6.1.3). CD31+/CD144+ iECs were separated by FACS and subsequently cultured in EGM2 including 10 µM SB431542 using plates coated with 1% gelatin.

As illustrated in FIG. 2, the result confirmed that CD31/CD144 positive cells were reproducibly prepared, and the cells were produced at a ratio of about 1.4% to about 7%.

Embodiment 3

Examination of the Characteristics of the Expanded iEC Through Subculture

After expansion CD31/CD144 positive cells (iEC) sorted by FACS, expression of VE-cadherin was examined by immunofluorescence, and ac-LDL uptake and tube formation were examined.

3-1. Examination of Expression of VE-Cadherin by Immunofluorescence Staining

Cells were fixed with 100% methanol for five minutes and permeabilized with 0.1% Triton X-100 for three minutes. Non-specific protein binding sites were blocked with 5% BSA for one hour. Cells were reacted with VE-cadherin (1:100, cell signaling) primary antibody and washed three times with PBS. Further, the cells were reacted with the secondary antibody with which Cy 3 (Millipore) was combined for two hours. Lastly, all slides were counterstained with 1 µg/ml DAPI (Sigma). The images were obtained with a confocal microscope (Zeiss LSM 510 Meta with LSM image examiner software, Germany).

3-2. Analysis of In Vitro Endothelial Cell Function ac-LDL uptake by adherent cells, which is one of the major features of the endothelial cell line was measured (Murohara et al., J. Clin. Invest., 2000). Cells cultured in gelatin-coated chamber slides for 24 hours were reacted at 37° C. for four hours in medium including 15 µg/ml DiI-labeled acetyl-low density lipoprotein (DiI-ac-LDL, Molecular Probes, Eugene, Oreg.). After washing, the samples were observed with a fluorescence microscope and an inverted phase microscope, and three fields were randomly selected and photographed.

3-3. Analysis of Tube (Vascular) Formation

Refrigerated Matrigel (150 µl, BD Bioscience) was placed in a precooled 48-well plate and incubated at 37° C. for 30 minutes. HUVECs, MSC, and iEC were dispensed onto solidified Matrigel ($2\times10^4$ cells/well) and cultured in EGM for 20 hours. Then, tube formation was photographed.

As illustrated in FIG. 3, the result confirmed that VE-cadherin was expressed at the cell interface in the expanded iEC and could take up the DiI-labeled ac-LDL, similarly to the HUVEC cells, which is completely different from MSC and has the ability to form a tube.

Embodiment 4

Optimal Gene Combinations for the Conversion of Wharton's Jelly Mesenchymal Stem Cells (WJ-MSC) into Endothelial Cells The present inventors conducted the following experiments to identify the optimal genes required for conversion of mesenchymal stem cells into endothelial cells, which was confirmed by the results of Embodiments as described above.

Endothelial cell differentiation potency was examined for a group in which four genes, Oct4, Nanog, Tal1, and LMO2, which were used in Embodiments as described above, were introduced; a group in which three genes, Oct4, Tal1 and LMO2 (OTL) were introduced; a group in which three genes, Nanog, Tal1 and LMO2 (NTL) were introduced; and a group in which three genes, Oct4, Nanog, and LMO2 (ONL) were introduced. Specifically, a combination of three genes, Oct4, Tal1 and LMO2 (OTL), Nanog, Tal1, and LMO2 (NTL) or Oct4, Nanog, and LMO2 (ONL) were introduced into cells, and after 24 hours, the cells were exchanged with fresh DMEM medium added with penicillin/streptomycin. The cells were cultured for two days and then subjected to cell selection for ten days to isolate transduced cells. Then, the cells were cultured in endothelial cell growth medium EGM2 including 10 µM SB431542 on a gelatin-coated dish. The cells were cultured for 21 days while replacing the medium every two days, and then subjected to FACS analysis.

As illustrated in FIG. 4, the results confirmed that four genes including Oct4, Nanog, Tal1, and LMO2 were introduced to convert into CD31/CD144 positive cells, but CD31/CD144 positive cells could not be obtained when a combination of three genes was introduced (See FIG. 4A). Even in the case of conducting an additional repeated experiment, CD31/CD144 positive cells were obtained at high efficiency (~5%) when four genes were simultaneously introduced, but CD31/CD144 positive cells hardly appeared when a combination of three genes, Nanog, Tal1, and LMO2 was introduced (See FIG. 4B).

As a result, the present inventors confirmed that four transcription factors such as Oct4, Nanog, Tal1, and LMO2 are required for efficient conversion of MSC into endothelial cells under the differentiation culture conditions of the present experiment. It was confirmed that the endothelial cell conversion did not occur in the absence of one gene among them.

The present invention has been mainly described above with reference to preferred embodiments thereof. It will be understood by those skilled in the art that various changes in form and details may be made therein without departing from the fundamental scope of the present invention. Therefore, the disclosed embodiments should be considered in an illustrative rather than a restrictive aspect. The scope of the present invention is defined by the appended claims instead of the foregoing description, and all differences within the scope of equivalents thereof should be construed as being included in the present invention.

The invention claimed is:

1. An in vitro method for converting mesenchymal stem cells into endothelial cells, the method comprising the steps of:
   (a) introducing lentiviral vectors comprising Oct4, Nanog, Tal1, and LMO2 genes into the mesenchymal stem cells; and
   (b) culturing the transduced mesenchymal stem cells on a gelatin-coated plate under culture conditions comprising endothelial cell growth medium EGM2 and SB431542, wherein said culturing induces the conversion of the mesenchymal stem cells into endothelial cells.

2. The method of claim 1, wherein the Oct4 gene comprises SEQ ID NO: 1, the Nanog gene comprises SEQ ID NO: 2, the Tal1 gene comprises SEQ ID NO: 3, and the LMO2 gene comprises SEQ ID NO: 4.

* * * * *